(12) United States Patent
Hoelz et al.

(10) Patent No.: US 6,739,333 B1
(45) Date of Patent: May 25, 2004

(54) STAINLESS STEEL CANISTER FOR PROPELLANT-DRIVEN METERING AEROSOLS

(75) Inventors: Hubert Hoelz, Oberheimbach (DE); Richard Thomas Lostritto, Gaithersburg, MD (US); Juergen Nagel, Bad Kreuznach (DE); Julio César Vega, Buenos Aires (AR)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/580,246

(22) Filed: May 26, 2000

Related U.S. Application Data
(60) Provisional application No. 60/167,772, filed on Nov. 29, 1999.

(30) Foreign Application Priority Data

May 26, 1999 (DE) .......................................... 199 24 098

(51) Int. Cl.$^7$ ............................................. A61M 11/00
(52) U.S. Cl. ............................. 128/200.23; 128/203.12; 239/338; 420/49; 420/52; 420/582
(58) Field of Search ................. 128/203.12, 200.14, 128/200.23; 239/338; 420/49, 52, 582

(56) References Cited

U.S. PATENT DOCUMENTS 3,645,725 A * 2/1972 Denhard et al. ............... 420/44
3,837,846 A * 9/1974 Becker et al. ................. 420/41
4,944,433 A   7/1990 Knecht et al.
5,513,767 A * 5/1996 Daehn ......................... 220/612

FOREIGN PATENT DOCUMENTS

| DE | 37 36 579 C2 | 5/1991 |
| DE | 195 04 502 A1 | 8/1996 |
| DE | 692 18 455 T2 | 3/1997 |
| DE | 694 12 626 T2 | 8/1998 |
| EP | 0 617 610 B1 | 3/1997 |
| EP | 0 708 805 B1 | 8/1998 |
| EP | 0 726 864 B1 | 3/1999 |
| HU | 177445 | 9/1982 |
| WO | WO 00 30607 A1 | 6/2000 |
| WO | WO 00 30608 A1 | 6/2000 |

OTHER PUBLICATIONS

Lewis, D. et al.; "Pressurized Metered Dose Inhalers (MDI)"; U.S. 2003/0066525 A1; Apr. 10, 2003.

Lewis, D. et al.; "Pressurised Metered Dose Inhaler (MDI)"; U.S. Pub. No. 2003/0089369 A1; May 15, 2003.

* cited by examiner

Primary Examiner—Weilun Lo
Assistant Examiner—Mital Patel
(74) Attorney, Agent, or Firm—Robert P. Raymond; Philip I. Datlow; Anthony P. Bottino

(57) ABSTRACT

The present invention relates to corrosion resistant stainless steel canisters for propellant-containing aerosol forumlations for use in propellant gas-operated inhalers.

58 Claims, 2 Drawing Sheets

STAINLESS STEEL CANISTER FOR PROPELLANT-DRIVEN METERING AEROSOLS

This application claims benefit of provisional application Ser. No. 60/167,772 filed Nov. 29, 1999.

The present invention relates to corrosion-resistant stainless steel canisters for propellant gas-containing aerosol formulations for use in propellant gas-operated inhalers.

BACKGROUND OF THE INVENTION

In propellant-driven inhalers, the active substances are stored together with the propellant in cartridge-like canisters. These canisters generally consist of an aluminium container sealed with an aluminium valve cup in which a valve is embedded. A canister of this kind can then be placed in the inhaler in the manner of a cartridge and is either left there permanently or replaced with a new cartridge after use. Since chlorofluorocarbons (CFCs) were proscribed on the grounds of their ozone-destroying properties at the Rio de Janeiro Conference at the beginning of the 90s, the use of fluorohydrocarbons (FHC) is promoted as an alternative for use in propellant-driven inhalers. The most promising example to date are TG 134a (1,1,1,2-tetrafluoroethane) and TG 227 (1,1,1,2,3,3,3-heptafluoropropane). Accordingly, existing systems of delivery for treatments by inhalation have had to be converted to CFC-free propellants and new delivery systems and active substance formulations have had to be developed.

Surprisingly, it has been found that aluminium canisters are not always resistant to drug formulations containing fluorohydrocarbons as propellants but have a high risk of corrosion depending on the composition of the formulations. This is particularly true of formulations which contain electrolytes and/or free ions, particularly free halides. In these cases, the aluminium is attacked, which means that aluminium cannot be used as a casing material for the canisters. Similar instabilities in the aluminium canisters have been observed when fluorohydrocarbons are used as propellants if the formulations contain acid or basic components, e.g. in the form of the active substances, the additives, in the form of stabilisers, surfactants, flavour enhancers, antioxidants, etc.

DESCRIPTION OF THE INVENTION

One of the tasks of the present invention is to provide a canister for propellant-driven inhalers which is corrosion-resistant in the presence of active substance formulations for inhalation therapy containing a fluorohydrocarbon as propellant, which has sufficient compressive and breaking strength to withstand processing and use, which ensures the quality of the formulations stored therein and overcomes the other disadvantages known from the prior art.

The invention solves this problem by providing a canister for propellant-driven inhalers which consists predominantly of an alloy which is corrosion-resistant in the presence of drug formulations containing fluorohydrocarbons. The components of this alloy contain chromium (Cr), nickel (Ni), molybdenum (Mo), iron (Fe) and carbon (C). In another embodiment the alloy additionally contains copper (Cu), manganese (Mn) and silicon (Si). The canister according to the invention consists of a container (2) and a valve cup (8) with valve (9). The container preferably consists of one of the alloys described below. The invention therefore also relates to a container of this kind.

The invention further relates to the use of a container or canister of this kind consisting of a container (2) and a valve cup (8) with valve (9) in propellant-operated metering aerosols (inhalers) and a process for producing them.

The invention is hereinafter explained more fully with reference to FIGS. 1 and 2.

Figure 1:
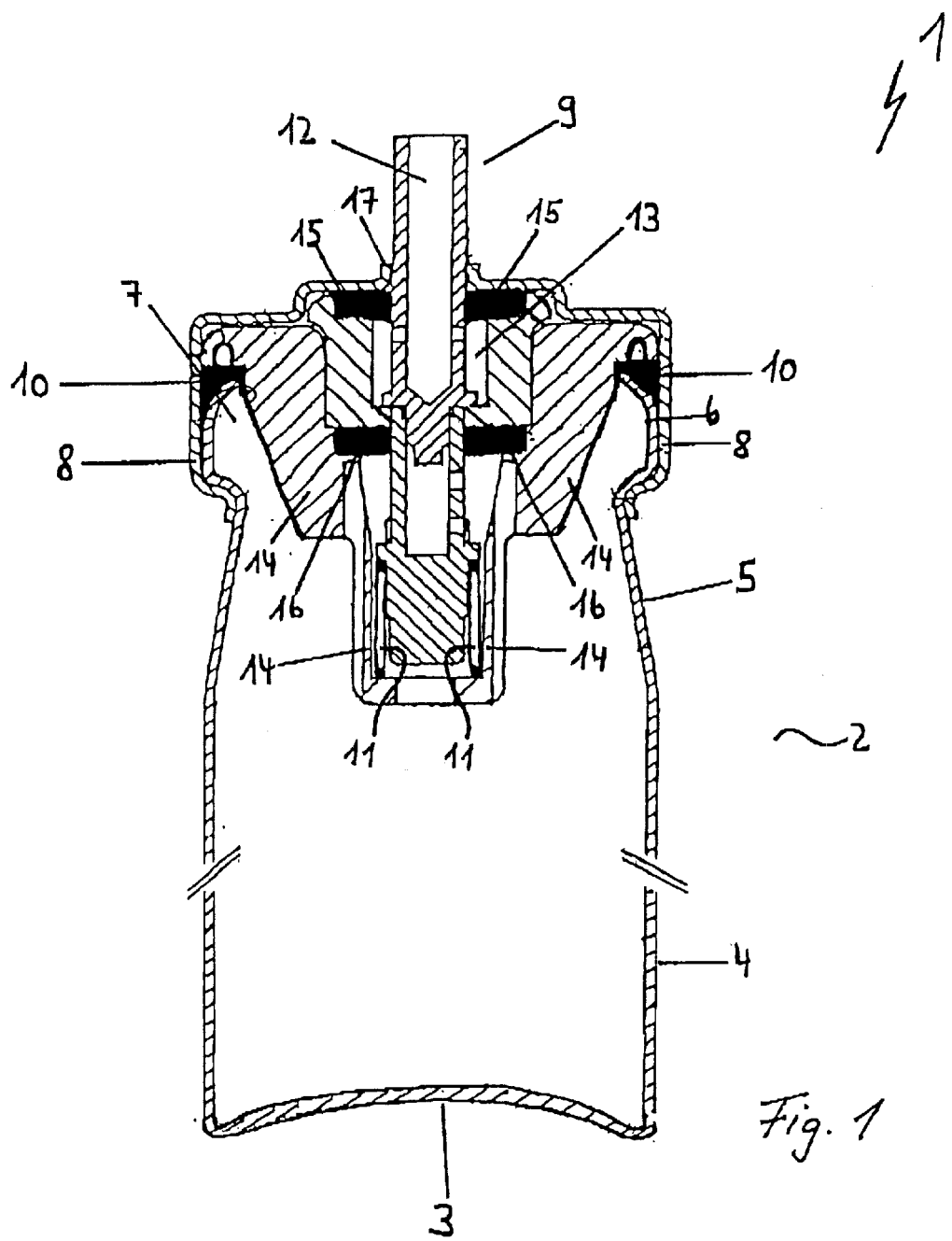
FIG. 1 shows the canister consisting of container (2), valve cup (8) and the valve (9) in cross-section.

FIG. 1 shows the canister (1) according to the invention in cross-section. The canister (1) consists of a container (2) for holding the pharmaceutical formulation and a valve cup (8) with valve (9). The shape and dimensions of the canister correspond to those of the aluminium canisters known from the prior art.

The container (2) according to the invention is made of an alloy having a content of Iron (Fe) of 40.0–53.0%,
Nickel (Ni) of 23.0–28.0%,
Chromium (Cr) of 19.0–23.0%,
Molybdenum (Mo) of 4.0–5.0%,
Manganese (Mn) of 0.0–2.0%,
Copper (Cu) of 1.0–2.0%,
Silicon (Si) 0.0–1.0%,
Phosphorus (P) 0.0–0.045%,
Sulfur (S) 0.0–0.035% and
Carbon (C) 0.0–0.020%.

This alloy is one according to the material number 1.4539 of the steel-iron-list of the association of the German iron-works-worker (in German language: Werkstoffnummer der Stahl-Eisen-Liste des Vereins deutscher Eisenhüttenleute).

A preferred alloy of this type has the following composition:

Chromium (Cr) 19.0–21.0%,
Nickel (Ni) 24.0–26.0%,
Molybdenum (Mo) 4.0–5.0%,
Copper (Cu) 1.0–2.0%,
Manganese (Mn) up to 2.0%,
Silicon (Si) up to 0.5% and
Carbon (C) up to 0.02%, whereby the remainder consists essentially of iron.

For a nearly identical alternative alloy the content of Molybdenum is limited to 4.5–5.0%.

In an alternative embodiment the container (2) according to the invention consists of an alloy according to the material number 1.4404 of the steel-iron-list of the association of the German iron-works-worker (in German language: Werkstoffnummer der Stahl-Eisen-Liste des Vereins deutscher Eisenhüttenleute)consisting of Iron (Fe) 60.0–72.0%,
Nickel (Ni) 9.0–13.0%,
Chromium (Cr) 17.0–21.0%,
Molybdenum (Mo) 2.0–3.0%,
Manganese (Mn) 0.0–1.5%,
Silicon (Si) 0.0–1.5%,
Phosphorus (P) 0.0–0.04%,
Sulfur (S) 0.0–0.04% and
Carbon (C) 0–0.03%.

Another embodiment of the canister (2) consists of an alloy consisting of:

Chromium (Cr) 16.5–18.5%,
Nickel (Ni) 11.0–14.0%,

Molybdenum (Mo) 2.0–2.5%,

Carbon (C) up to 0.03% and iron as the remaining component.

The alloys mentioned above are such that they are corrosion-resistant to various liquefied fluorohydrocarbons such as TG 134a (1,1,1,2-tetrafluoroethane) and TG 227 (1,1,1,2,3,3,3-heptafluoropropane). These include propellant gas formulations having active substances suitable for inhalation therapy, surfactants, cosolvents, stabilisers, complexing agents, flavour correctors, antioxidants, salts, acids, bases or electrolytes, such as hydroxide ions, cyanide ions and/or halide anions such as fluoride, chloride, bromide or iodide.

The container (2) is formed from a casing made of one of the alloys described above. The container (2) has four different zones: the flat or concave, inwardly domed base (3), a cylindrical portion (4) which merges into the tapering neck (5) in its upper third and finally ends in the bead (6) which encircles the opening (7) of the container.

The wall thickness of the container (2) is between 0.1 and 0.5 mm in a preferred embodiment, preferably between 0.15 and 0.35 mm, most preferably about 0.19 to 3.0 mm.

In a preferred embodiment the container (2) will withstand a bursting pressure of more than 30000 hPa, preferably more than 100000 hPa, most preferably more than 200000 hPa. The weight of the container (2) is 5–15 g in a preferred embodiment, 7–10 g in another and 7.9–8.7 g in yet another. In an equally preferred embodiment the container (2) has a volume of 5 to 50 ml. Other containers have a volume of 10 to 20 ml whilst still others have volumes of about 15–18 ml.

In the sealed state the container (2) is tightly sealed by means of the valve cup (8) after being filled with the pharmaceutical formulation and the propellant.

In another embodiment the valve cup (8) also consists of corrosion-resistant material. Preferably this is one of the alloys described above for the containers and/or a plastics material of suitable pharmaceutical quality.

In another embodiment the valve cup (8) consists of aluminium. In this case the seal (10) and/or the valve (9) are constructed so that the valve cup (8) itself cannot come into contact with the liquid inside the container.

A preferred embodiment of the valve cup (8) is as described in GB 2324121, to which reference is hereby made.

In the closed state of the canister, the valve cup (8) is crimped around the container (2) at its bead (6). In preferred embodiments a seal or gasket (10) seals the valve cup (8) relative to the bead (6). The seal may be annular or disc shaped. It is preferably disc shaped. It may consist of materials known from the prior art which are suitable for using pharmaceutical formulations with fluorohydrocarbons as the propellants. Examples of suitable materials include thermoplasts, elastomers, materials such as neoprene, isobutylene, isoprene, butyl rubber, buna rubber, nitrile rubber, copolymers of ethylene and propylene, terpolymers of ethylene, propylene and a diene, e.g. butadiene, or fluorinated polymers. The preferred materials are ethylene/propylene/diene terpolymers (EPDM).

On the side of the valve cup (8) facing the inside of the container, a valve (9) is formed so that the valve stem (12) passes through the valve cup (8) to the other side. The valve (9) sits in the central opening of the gasket (10) to form a seal. The gasket (10) and valve (9) together seal the valve cup (8) from the inside of the container, so that it cannot come into contact with the liquid in the container (2).

The valve (9) is constructed so that every element which is capable of coming into contact with the liquid inside the container (2) consists of a material which is corrosion-resistant with respect to this liquid. Such elements include for example the spring or springs (11), the valve stem (12), which projects from the inside to the outside through the opening (17) in the valve cup (8), the metering chamber (13) and the valve body (14). The spring (11) consists of steel, preferably a stainless steel. The other elements of the valve (9) may consist, for example, of steel, the alloy described above and/or a plastic. The elements (12), (13) and (14) preferably consist of a plastic, particularly a polyester, most preferably polybutylene terephthalate.

As shown in FIG. 1, one or more other gaskets or seals, e.g. the gaskets (15) and/or (16), may be provided to prevent liquid or gas from escaping outwards from the inside of the container. The gasket or gaskets may be arranged so that the liquid inside the container comes into contact only with the container jacket and the valve, apart from the actual gasket or gaskets.

The gasket (15) seals off the valve stem, which is optionally vertically movable, at the point where it penetrates the valve cup (8). The gasket (16) seals the valve stem (12) inside the valve relative to the valve body (14) and/or the metering chamber (13). In this way, the gaskets (15) and (16) prevent any liquid or gas from escaping from the interior of the container along the outer casing of the valve stem and out of the canister or from coming into contact with the valve cup by this route. The gaskets (15) and (16) may be made of the same material as the gasket (10), preferably an ethylene/propylene/diene terpolymer.

In one embodiment in which the valve cup (8) is not made of aluminium but of one of the corrosion-resistant materials described above, it is not necessary for the gasket (10) together with the valve (9) to isolate the valve cup completely from the inside of the container. Therefore, it is not necessary in this case for the gasket (10) and valve (9) to be in sealing contact with one another. There may be a gap between the gasket (10) and the valve (9). In such a case the gasket (10) sits directly on the underside of the valve cup (8), for example, and seals the edge of the valve cup (8) relative to the bead (6) on the container. The gasket (15) then seals the opening (17) in the valve cup (8) from the interior of the container.

Figure 2:
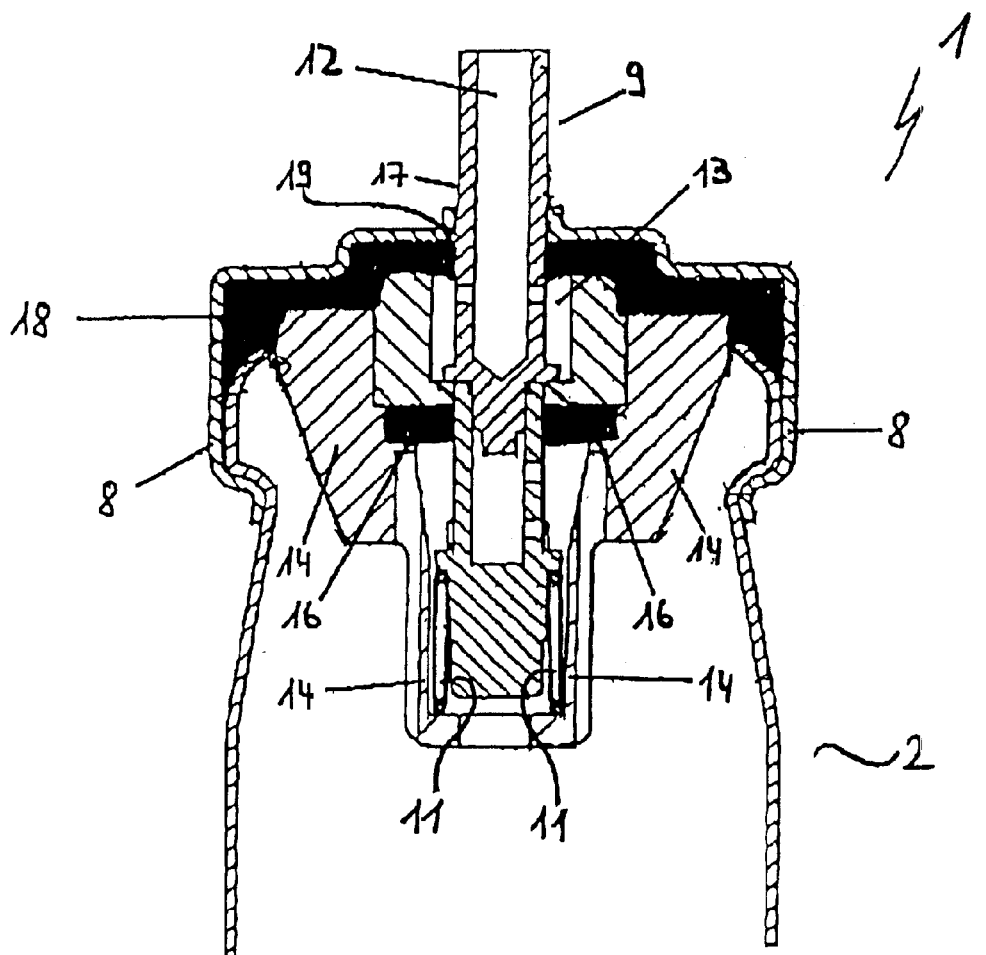
FIG. 2 shows another embodiment of the valve cup (8) and the valve (9) in cross-section.

FIG. 2 shows another embodiment of the valve cup (8) with embedded valve (9). This embodiment is largely identical to that in FIG. 1. The major difference is that the gasket (10) and the gasket (16) in the embodiment in FIG. 2 are combined to form one gasket (18). The gasket (18) encloses the underside of the valve plate (18). It is arranged so that the valve body (14) is embedded in the gasket. The valve stem (12) passes through the gasket via the opening (19) which is located directly below the opening (17) in the valve cup (8). The opening (19) is of such dimensions as to seal the valve stem (12) relative to the valve cup (8). The sealing material for the gasket (18) is identical to that described for the gasket (10).

The container (2) according to the invention is produced analogously to the processes known from the prior art for producing aluminium canisters and the like, in which the container is stamped out of a sheet of the material in question, or the corresponding alloy. In the present invention, the container (2) is stamped out of a sheet of the above-mentioned alloys of chromium (Cr), nickel (Ni), molybdenum (Mo), iron (Fe) and carbon (C) or from an alloy which additionally contains copper (Cu), manganese (Mn) and silicon (Si).

The container (2) or canister consisting of container (2) and valve cup (8) with valve (9) according to the invention is particularly suitable for use with propellant gas formulations containing fluorohydrocarbons. Propellant gas formulations which can preferably be used in conjunction with the invention are disclosed in WO 94/13262, to which reference is hereby made. Particularly preferred formulations disclosed therein are acid-stabilised and/or ethanol propellant gas formulations containing 1,1,2,2-tetrafluoroethane (TG 134a) and/or 1,1,1,2,3,3,3-heptafluoropropane (TG 227) as the propellant gas, particularly those which contain ipatropium bromide, oxitropium bromide, albuterol, tiotropium bromide or fenoterol as active substance.

Depending on the active substance, inorganic or organic acids may be used as stabilisers. Examples of inorganic acids include, in addition to halic acids and other mineral acids: sulphuric acid, hydrochloric acid, nitric acid or phosphoric acid, whilst examples of organic acids include ascorbic acid or citric acid. In the case of the salts of the active substances, the preferred acids are those wherein the anion is identical to that of the salt of the active substance. Citric acid is generally suitable for all active substances and their salts and is also most preferred.

The acid content is such that the pH of the formulation is between 1.0 and 7.0, preferably between 2.0 and 5.0 and most preferably at about 3.5. In the case of inorganic acids the preferred acid content is in the range from about 0.00002 to 0.01 N. In the case of ascorbic acid the preferred content is roughly in the range from 0.0045 to 5.0 mg/ml and in the case of citric acid it is within the range from 0.0039 to 27.7 mg/ml.

The formulations may additionally contain ethanol as cosolvent. The preferred amount is 1.0 to 50.0% by weight of the formulation.

The following are some preferred formulations by way of example which can be stored in a canister or a container of the type described above:

EXAMPLE 1

| | |
|---|---|
| Ipatropium bromide monohydrate | 0.001–2.5% by weight |
| Absolute ethanol | 0.001–50% by weight |
| TG 134a | 50.0–99.0% by weight |
| Inorganic acid | 0.01–0.00002 normal |
| Water | 0.0–5.0% by weight |

EXAMPLE 2

| | |
|---|---|
| Ipatropium bromide monohydrate | 0.001–2.5% by weight |
| Absolute ethanol | 0.001–50% by weight |
| TG 134a | 50.0–99.0% by weight |
| Ascorbic acid | 0.00015–5.0 mg/ml |
| purified water | 0.0–5.0% by weight |

EXAMPLE 3

| | |
|---|---|
| Ipatropium bromide monohydrate | 0.0187% by weight |
| Absolute ethanol | 15.0000% by weight |
| TC 134a | 84.47730% by weight |
| Citric acid | 0.0040% by weight |
| purified water | 0.5000% by weight |
| Total | 100.0000% by weight |

EXAMPLE 4

| | |
|---|---|
| Ipatropium bromide monohydrate | 0.0374% by weight |
| Absolute ethanol | 15.0000% by weight |
| TG 134a | 84.4586% by weight |
| Citric acid | 0.0040% by weight |
| purified water | 0.5000% by weight |
| Total | 100.0000% by weight |

EXAMPLE 5

| | |
|---|---|
| Ipatropium bromide monohydrate | 0.0748% by weight |
| Absolute ethanol | 15.0000% by weight |
| TG 134a | 84.4212% by weight |
| Citric acid | 0.0040% by weight |
| Purified water | 0.5000% by weight |
| Total | 100.0000% by weight |

EXAMPLE 6

| | |
|---|---|
| Fenoterol hydrobromide | 0.192% by weight |
| Absolute ethanol | 30.000% by weight |
| TG 134a | 67.806% by weight |
| Citric acid | 0.002% by weight |
| Purified water | 2.000% by weight |
| Total | 100.0000% by weight |

A method of filling the canisters with the corresponding formulation might be, for example, the dual stage pressure fill method, the single stage cold fill method or the single stage pressure fill method.

What is claimed is:

1. A metered-dose inhaler having a metal cannister to hold drug and non-CFC propellant gas, comprising the following alloy forming walls of the cannister:

Iron comprising about 40.0 to about 53.0%,

Nickel comprising about 23.0 to about 28.0%,

Chromium comprising about 19.0 to about 23.0%,

Molybdenum of about 4.0 to about 5.0%,

Manganese of about 0.0 to about 2.0%,

Copper of about 1.0 to about 2.0%,

Silicon of about 0.0 to about 1.0%,

Phosphorous of about 0.0 to about 0.045%,

Sulfur of about 0.0 to about 0.035% and

Carbon of about 0.0 to about 0.020%.

2. The metered-dose inhaler as recited in claim 1, wherein the alloy is as follows:

Chromium about 19.0 to about 21.0%,

Nickel about 24.0 to about 26.0%,

Molybdenum about 4.0 to about 5.0%,

Copper about 1.0 to about 2.0%,

Manganese about 0.0 to about 2.0%,

Silicon about 0.0 to about 0.5%,

Carbon about 0.0 to about 0.02% and remainder Iron.

3. The metered-dose inhaler as recited in claim 1, wherein the cannister comprises a container and a valve cup with a valve embedded therein, the container constituting walls of the cannister.

4. The metered-dose inhaler as recited in claim 3, wherein the valve cup is aluminum and is sealed with a gasket relative to the interior of the container.

5. The metered-dose inhaler as recited in claim 3, wherein the valve contains one or more stainless steel springs, a valve stem, a metering chamber and a valve body, wherein one or more of the valve stem, the metering chamber and the valve body are made of material selected from steel, the alloy used for forming walls of the cannister and a plastic.

6. The metered-dose inhaler as recited in claim 5, wherein the springs are made of stainless steel, and the valve stem, the metering chamber and the valve body are made of polybutylene terephthalate.

7. The metered-dose inhaler as recited in claim 5, wherein the valve stem is sealed off from the valve cup by a gasket or gaskets.

8. The metered-dose inhaler as recited in claim 7, wherein the gasket or gaskets are made from ethylene/propylene/diene terpolymer.

9. The metered-dose inhaler as recited in claim 5, wherein the valve cup is made from the alloy used to form the container.

10. The metered-dose inhaler as recited in claim 1, wherein walls of the canister can withstand a bursting pressure of more than 30,000 hPa.

11. The metered-dose inhaler as recited in claim 10, wherein walls of the cannister can withstand a bursting pressure of more than 100,000 hPa.

12. The metered-dose inhaler as recited in claim 10, wherein walls of the cannister can withstand a bursting pressure of more than 200,000 hPa.

13. The metered-dose inhaler as recited in claim 1, wherein walls of the cannister are about 0.1 to about 0.5 mm thick.

14. The metered-dose inhaler as recited in claim 13, wherein walls of the cannister are about 0.15 to about 0.35 mm thick.

15. The metered-dose inhaler as recited in claim 14, wherein walls of the cannister are about 0.19 to about 0.30 mm thick.

16. A metered-dose inhaler according to claim 1, wherein the cannister contains a formulation comprising a fluorohydrocarbon propellant.

17. A metered-dose inhaler according to claim 16, wherein the fluorohydrocarbon propellant is selected from 1,1,1,2-tetrafluoroethane and 1,1,1,2,3,3,3-heptafluoropropane.

18. A metered-dose inhaler according to claim 16, wherein the formulation further comprises one or more electrolytes.

19. A metered-dose inhaler according to claim 16, wherein the formulation further comprises one or more acids.

20. A metered-dose inhaler according to claim 16, wherein the formulation further comprises ethanol.

21. A metered-dose inhaler having a metal cannister to hold drug and non-CFC propellant gas, comprising the following alloy forming walls of the cannister:
Iron about 60.0 to about 72.0%,
Nickel about 9.0 to about 13.0%,
Chromium about 17.0 to about 21.00%,
Molybdenum about 2.0 to about 3.0%,
Manganese about 0.0 to about 1.5%,
Silicon about 0.0 to about 1.5%,
Phosphorous about 0.0 to about 0.04%,
Sulfur about 0.0 to about 0.04% and
Carbon about 0.0 to about 0.03%.

22. The metered-dose inhaler as recited in claim 21, wherein the cannister comprises a container and a valve cup with a valve embedded therein, the container constituting walls of the cannister.

23. The metered-dose inhaler as recited in claim 22, wherein the valve cup is aluminum and is sealed with a gasket relative to the interior of the container.

24. The metered-dose inhaler as recited in claim 22, wherein the valve contains one or more stainless steel springs, a valve stem, a metering chamber and a valve body, wherein one or more of the valve stem, the metering chamber and the valve body are made of material selected from steel, the alloy used for forming walls of the cannister and a plastic.

25. The metered-dose inhaler as recited in claim 24, wherein the springs are made of stainless steel, and the valve stem, the metering chamber and the valve body are made of polybutylene terephthalate.

26. The metered-dose inhaler as recited in claim 24, wherein the valve stem is sealed off from the valve cup by a gasket or gaskets.

27. The metered-dose inhaler as recited in claim 26, wherein the gasket or gaskets are made from ethylene/propylene/diene terpolymer.

28. The metered-dose inhaler as recited in claim 24, wherein the valve cup is made from the alloy used to form the container.

29. The metered-dose inhaler as recited in claim 21, wherein walls of the canister can withstand a bursting pressure of more than 30,000 hPa.

30. The metered-dose inhaler as recited in claim 29, wherein walls of the cannister can withstand a bursting pressure of more than 100,000 hPa.

31. The metered-dose inhaler as recited in claim 29, wherein walls of the cannister can withstand a bursting pressure of more than 200,000 hPa.

32. The metered-dose inhaler as recited in claim 21, wherein walls of the cannister are about 0.1 to about 0.5 mm thick.

33. The metered-dose inhaler as recited in claim 32, wherein walls of the cannister are about 0.15 to about 0.35 mm thick.

34. The metered-dose inhaler as recited in claim 33, wherein walls of the cannister are about 0.19 to about 0.30 mm thick.

35. A metered-dose inhaler according to claim 21, wherein the cannister contains a formulation comprising a fluorohydrocarbon propellant.

36. A metered-dose inhaler according to claim 35, wherein the fluorohydrocarbon is selected from 1,1,1,2-tetrafluoroethane and 1,1,1,2,3,3,3-heptafluoropropane.

37. A metered-dose inhaler according to claim 35, wherein the formulation further comprises one or more electrolytes.

38. A metered-dose inhaler according to claim 35, wherein the formulation further comprises one or more acids.

39. A metered-dose inhaler according to claim 35, wherein the formulation further comprises ethanol.

40. A metered-dose inhaler having a metal cannister to hold drug and non-CFC propellant gas, comprising the following alloy forming walls of the cannister:
Chromium about 16.5 to about 18.5%,
Nickel about 11.0 to about 14.0%,
Molybdenum about 2.0 to about 2.5%,
Carbon about 0.0 to about 0.03% and remainder Iron.

41. The metered-dose inhaler as recited in claim 40, wherein the cannister comprises a container and a valve cup with a valve embedded therein, the container constituting walls of the cannister.

42. The metered-dose inhaler as recited in claim 41, wherein the valve cup is aluminum and is sealed with a gasket relative to the interior of the container.

43. The metered-dose inhaler as recited in claim 41, wherein the valve contains one or more stainless steel springs, a valve stem, a metering chamber and a valve body, wherein one or more of the valve stem, the metering chamber and the valve body are made of material selected from steel, the alloy used for forming walls of the cannister and a plastic.

44. The metered-dose inhaler as recited in claim 43, wherein the springs are made of stainless steel, and the valve stem, the metering chamber and the valve body are made of polybutylene terephthalate.

45. The metered-dose inhaler as recited in claim 43, wherein the valve stem is sealed off from the valve cup by a gasket or gaskets.

46. The metered-dose inhaler as recited in claim 45, wherein the gasket or gaskets are made from ethylene/propylene/diene terpolymer.

47. The metered-dose inhaler as recited in claim 43, wherein the valve cup is made from the alloy used to form the container.

48. The metered-dose inhaler as recited in claim 40, wherein walls of the canister can withstand a bursting pressure of more than 30,000 hPa.

49. The metered-dose inhaler as recited in claim 48, wherein walls of the cannister can withstand a bursting pressure of more than 100,000 hPa.

50. The metered-dose inhaler as recited in claim 48, wherein walls of the cannister can withstand a bursting pressure of more than 200,000 hPa.

51. The metered-dose inhaler as recited in claim 40, wherein walls of the cannister are about 0.1 to about 0.5 mm thick.

52. The metered-dose inhaler as recited in claim 51, wherein walls of the cannister are about 0.15 to about 0.35 mm thick.

53. The metered-dose inhaler as recited in claim 52, wherein walls of the cannister are about 0.19 to about 0.30 mm thick.

54. A metered-dose inhaler according to claim 40, wherein the cannister contains a formulation comprising a fluorohydrocarbon propellant.

55. A metered-dose inhaler according to claim 54, wherein the fluorohydrocarbon is selected from 1,1,1,2-tetrafluoroethane and 1,1,1,2,3,3,3-heptafluoropropane.

56. A metered-dose inhaler according to claim 54, wherein the formulation further comprises one or more electrolytes.

57. A metered-dose inhaler according to claim 54, wherein the formulation further comprises one or more acids.

58. A metered-dose inhaler according to claim 54, wherein the formulation further comprises ethanol.

* * * * *

UNITED STATES PATENT AND TRADEMARK OFFICE
CERTIFICATE OF CORRECTION

PATENT NO. : 6,739,333 B1
DATED : May 25, 2004
INVENTOR(S) : Hubert Hoelz et al.

It is certified that error appears in the above-identified patent and that said Letters Patent is hereby corrected as shown below:

Column 5,
Lines 9-10, please delete "ipatropium" and insert -- ipratropium --.
Lines 40, 50 and 60, please delete "Ipatropium" and insert -- Ipratropium --.

Column 6,
Lines 5 and 16, please delete "Ipatropium" and insert -- Ipratropium --.

Column 10,
Line 27, please insert the following claims:
-- 59. A metered-dose inhaler according to claim 16, wherein the formulation further contains an active substance selected from ipratropium bromide, ipratropium bromide monohydrate, oxitropium bromide, albuterol, tiotropium bromide, fenoterol or fenoterol hydrobromide. --
-- 60. A metered-dose inhaler according to claim 35, wherein the formulation further contains an active substance selected from ipratropium bromide, ipratropium bromide monohydrate, oxitropium bromide, albuterol, tiotropium bromide, fenoterol or fenoterol hydrobromide. --
-- 61. A metered-dose inhaler according to claim 54, wherein the formulation further contains an active substance selected from ipratropium bromide, ipratropium bromide monohydrate, oxitropium bromide, albuterol, tiotropium bromide, fenoterol or fenoterol hydrobromide. --
-- 62. A metered-dose inhaler according to claim 59, where the active substance is ipratropium bromide monohydrate. --
-- 63. A metered-dose inhaler according to claim 60, where the active substance is ipratropium bromide monohydrate.--
-- 64. A metered-dose inhaler according to claim 61, where the active substance is ipratropium bromide monohydrate. --
-- 65. A metered-dose inhaler according to claim 1, wherein the cannister contains the following formulation having the following ingredients in the % by weights as indicated:

Ipratropium bromide monohydrate 0.001 -- 2.5% by weight;
Absolute ethanol 0.001 -- 50% by weight;
1,1,1,2 -- tetrafluoroethane 50.0 -- 99.0% by weight;
Inorganic acid 0.01 -- 0.00002 normal; and
Water 0.0 5.0% by weight. --

UNITED STATES PATENT AND TRADEMARK OFFICE
CERTIFICATE OF CORRECTION

PATENT NO. : 6,739,333 B1
DATED : May 25, 2004
INVENTOR(S) : Hubert Hoelz et al.

It is certified that error appears in the above-identified patent and that said Letters Patent is hereby corrected as shown below:

Column 10, (cont.)

-- 66. A metered-dose inhaler according to claim 1, wherein the cannister contains the following formulation having the following ingredients in the % by weights as indicated:

Ipratropium bromide monohydrate 0.001-- 2.5% by weight;
Absolute ethanol 0.001 -- 50% by weight;
1,1,1,2 – tetrafluoroethane 50.0 -- 99.0% by weight;
Ascorbic acid 0.00015 -- 5.0 mg/ml; and
Purified water 0.0 -- 5.0% by weight. --

-- 67. A metered-dose inhaler according to claim 1, wherein the cannister contains the following formulation having the following ingredients in the % by weights as indicated:

Ipratropium bromide monohydrate 0.0187 % by weight;
Absolute ethanol 15.0000% by weight;
1,1,1,2 – tetrafluoroethane 84.47730% by weight;
Citric acid 0.0040% by weight; and
Purified water 0.5000 % by weight. --

-- 68. A metered-dose inhaler according to claim 1, wherein the cannister contains the following formulation having the following ingredients in the % by weights as indicated:

Ipratropium bromide monohydrate 0.0374% by weight;
Absolute ethanol 15.0000% by weight;
1,1,1,2 – tetrafluoroethane 84.4586% by weight;
Citric acid 0.0040% by weight; and
Purified water 0.5000% by weight. --

UNITED STATES PATENT AND TRADEMARK OFFICE
CERTIFICATE OF CORRECTION

PATENT NO. : 6,739,333 B1
DATED : May 25, 2004
INVENTOR(S) : Hubert Hoelz et al.

It is certified that error appears in the above-identified patent and that said Letters Patent is hereby corrected as shown below:

Column 10, (cont.)
-- 69. A metered-dose inhaler according to claim 1, wherein the cannister contains the following formulation having the following ingredients in the % by weights as indicated:

Ipratropium bromide monohydrate 0.0748% by weight;
Absolute ethanol 15.0000% by weight;
1,1,1,2 – tetrafluoroethane 84.4212% by weight;
Citric acid 0.0040% by weight; and
Purified water 0.5000 % by weight. --

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,739,333 B1
DATED : May 25, 2004
INVENTOR(S) : Hubert Hoelz et al.

It is certified that error appears in the above-identified patent and that said Letters Patent is hereby corrected as shown below:

Title page,
Item [73], Assignee, please delete "Boehringer Ingelheim Pharma KG, Ingelheim (DE)" and insert -- Boehringer Ingelheim Pharma KG, Ingelheim (DE) and Boehringer Ingelheim Pharmaceuticals, Inc., Ridgefield, CT --.

Column 5,
Lines 9-10, please delete "ipatropium" and insert -- ipratropium --.
Lines 40, 50 and 60, please delete "Ipatropium" and insert -- Ipratropium --.

Column 6,
Lines 5 and 16, please delete "Ipatropium" and insert -- Ipratropium --.

Column 10,
Line 27, please insert the following claims:
-- 59. A metered-dose inhaler according to claim 16, wherein the formulation further contains an active substance selected from ipratropium bromide, ipratropium bromide monohydrate, oxitropium bromide, albuterol, tiotropium bromide, fenoterol or fenoterol hydrobromide. --
-- 60. A metered-dose inhaler according to claim 35, wherein the formulation further contains an active substance selected from ipratropium bromide, ipratropium bromide monohydrate, oxitropium bromide, albuterol, tiotropium bromide, fenoterol or fenoterol hydrobromide. --
-- 61. A metered-dose inhaler according to claim 54, wherein the formulation further contains an active substance selected from ipratropium bromide, ipratropium bromide monohydrate, oxitropium bromide, albuterol, tiotropium bromide, fenoterol or fenoterol hydrobromide. --
-- 62. A metered-dose inhaler according to claim 59, where the active substance is ipratropium bromide monohydrate. --
-- 63. A metered-dose inhaler according to claim 60, where the active substance is ipratropium bromide monohydrate.--
-- 64. A metered-dose inhaler according to claim 61, where the active substance is ipratropium bromide monohydrate. --

UNITED STATES PATENT AND TRADEMARK OFFICE
CERTIFICATE OF CORRECTION

PATENT NO.      : 6,739,333 B1
DATED           : May 25, 2004
INVENTOR(S)     : Hubert Hoelz et al.

It is certified that error appears in the above-identified patent and that said Letters Patent is hereby corrected as shown below:

<u>Column 10, (cont.)</u>
-- 65. A metered-dose inhaler according to claim 1, wherein the cannister contains the following formulation having the following ingredients in the % by weights as indicated:

Ipratropium bromide monohydrate 0.001 -- 2.5% by weight;
Absolute ethanol 0.001 -- 50% by weight;
1,1,1,2 -- tetrafluoroethane 50.0 -- 99.0% by weight;
Inorganic acid 0.01 --  0.00002 normal; and
Water 0.0  5.0% by weight. --

-- 66. A metered-dose inhaler according to claim 1, wherein the cannister contains the following formulation having the following ingredients in the % by weights as indicated:

Ipratropium bromide monohydrate 0.001-- 2.5% by weight;
Absolute ethanol 0.001 -- 50% by weight;
1,1,1,2 – tetrafluoroethane 50.0 -- 99.0% by weight;
Ascorbic acid 0.00015 --  5.0 mg/ml; and
Purified water 0.0 -- 5.0% by weight. --

-- 67. A metered-dose inhaler according to claim 1, wherein the cannister contains the following formulation having the following ingredients in the % by weights as indicated:

Ipratropium bromide monohydrate 0.0187 % by weight;
Absolute ethanol 15.0000% by weight;
1,1,1,2 – tetrafluoroethane 84.47730% by weight;
Citric acid 0.0040% by weight; and
Purified water 0.5000 % by weight. --

UNITED STATES PATENT AND TRADEMARK OFFICE
CERTIFICATE OF CORRECTION

PATENT NO.   : 6,739,333 B1
DATED        : May 25, 2004
INVENTOR(S)  : Hubert Hoelz et al.

It is certified that error appears in the above-identified patent and that said Letters Patent is hereby corrected as shown below:

Column 10, (cont.)
-- 68. A metered-dose inhaler according to claim 1, wherein the cannister contains the following formulation having the following ingredients in the % by weights as indicated:

Ipratropium bromide monohydrate 0.0374% by weight;
Absolute ethanol 15.0000% by weight;
1,1,1,2 – tetrafluoroethane 84.4586% by weight;
Citric acid 0.0040% by weight; and
Purified water 0.5000% by weight. --

-- 69. A metered-dose inhaler according to claim 1, wherein the cannister contains the following formulation having the following ingredients in the % by weights as indicated:

Ipratropium bromide monohydrate 0.0748% by weight;
Absolute ethanol 15.0000% by weight;
1,1,1,2 – tetrafluoroethane 84.4212% by weight;
Citric acid 0.0040% by weight; and
Purified water 0.5000 % by weight. --

Signed and Sealed this

Twenty-second Day of March, 2005

JON W. DUDAS
*Acting Director of the United States Patent and Trademark Office*

UNITED STATES PATENT AND TRADEMARK OFFICE
CERTIFICATE OF CORRECTION

PATENT NO.    : 6,739,333 B1
DATED         : May 25, 2004
INVENTOR(S)   : Hubert Hoelz et al.

It is certified that error appears in the above-identified patent and that said Letters Patent is hereby corrected as shown below:

Title page,
Item [73], Assignee, please delete "Boehringer Ingelheim Pharma KG, Ingelheim (DE)" and insert -- Boehringer Ingelheim Pharma KG, Ingelheim (DE) and Boehringer Ingelheim Pharmaceuticals, Inc., Ridgefield, CT --.

Column 5,
Lines 9-10, please delete "ipatropium" and insert -- ipratropium --.
Lines 40, 50 and 60, please delete "Ipatropium" and insert -- Ipratropium --.

Column 6,
Lines 5 and 16, please delete "Ipatropium" and insert -- Ipratropium --.

Column 10,
Line 27, please insert the following claims:
-- 59. A metered-dose inhaler according to claim 16, wherein the formulation further contains an active substance selected from ipratropium bromide, ipratropium bromide monohydrate, oxitropium bromide, albuterol, tiotropium bromide, fenoterol or fenoterol hydrobromide. --
-- 60. A metered-dose inhaler according to claim 35, wherein the formulation further contains an active substance selected from ipratropium bromide, ipratropium bromide monohydrate, oxitropium bromide, albuterol, tiotropium bromide, fenoterol or fenoterol hydrobromide. --
-- 61. A metered-dose inhaler according to claim 54, wherein the formulation further contains an active substance selected from ipratropium bromide, ipratropium bromide monohydrate, oxitropium bromide, albuterol, tiotropium bromide, fenoterol or fenoterol hydrobromide. --
-- 62. A metered-dose inhaler according to claim 59, where the active substance is ipratropium bromide monohydrate. --
-- 63. A metered-dose inhaler according to claim 60, where the active substance is ipratropium bromide monohydrate.--
-- 64. A metered-dose inhaler according to claim 61, where the active substance is ipratropium bromide monohydrate. --

UNITED STATES PATENT AND TRADEMARK OFFICE
CERTIFICATE OF CORRECTION

PATENT NO.    : 6,739,333 B1
DATED         : May 25, 2004
INVENTOR(S)   : Hubert Hoelz et al.

It is certified that error appears in the above-identified patent and that said Letters Patent is hereby corrected as shown below:

Column 10, (cont.)
-- 65. A metered-dose inhaler according to claim 1, wherein the cannister contains the following formulation having the following ingredients in the % by weights as indicated:

Ipratropium bromide monohydrate 0.001 -- 2.5% by weight;
Absolute ethanol 0.001 -- 50% by weight;
1,1,1,2 -- tetrafluoroethane 50.0 -- 99.0% by weight;
Inorganic acid 0.01 -- 0.00002 normal; and
Water 0.0-5.0% by weight. --

-- 66. A metered-dose inhaler according to claim 1, wherein the cannister contains the following formulation having the following ingredients in the % by weights as indicated:

Ipratropium bromide monohydrate 0.001-- 2.5% by weight;
Absolute ethanol 0.001 -- 50% by weight;
1,1,1,2 – tetrafluoroethane 50.0 -- 99.0% by weight;
Ascorbic acid 0.00015 -- 5.0 mg/ml; and
Purified water 0.0 -- 5.0% by weight. --

-- 67. A metered-dose inhaler according to claim 1, wherein the cannister contains the following formulation having the following ingredients in the % by weights as indicated:

Ipratropium bromide monohydrate 0.0187 % by weight;
Absolute ethanol 15.0000% by weight;
1,1,1,2 – tetrafluoroethane 84.47730% by weight;
Citric acid 0.0040% by weight; and
Purified water 0.5000 % by weight. --

-- 68. A metered-dose inhaler according to claim 1, wherein the cannister contains the following formulation having the following ingredients in the % by weights as indicated:

Ipratropium bromide monohydrate 0.0374% by weight;
Absolute ethanol 15.0000% by weight;
1,1,1,2 – tetrafluoroethane 84.4586% by weight;
Citric acid 0.0040% by weight; and
Purified water 0.5000% by weight. --

UNITED STATES PATENT AND TRADEMARK OFFICE
CERTIFICATE OF CORRECTION

PATENT NO. : 6,739,333 B1
DATED : May 25, 2004
INVENTOR(S) : Hubert Hoelz et al.

It is certified that error appears in the above-identified patent and that said Letters Patent is hereby corrected as shown below:

<u>Column 10, (cont.)</u>
-- 69. A metered-dose inhaler according to claim 1, wherein the cannister contains the following formulation having the following ingredients in the % by weights as indicated:

Ipratropium bromide monohydrate 0.0748% by weight;
Absolute ethanol 15.0000% by weight;
1,1,1,2 – tetrafluoroethane 84.4212% by weight;
Citric acid 0.0040% by weight; and
Purified water 0.5000 % by weight. --

-- 70. A metered-dose inhaler according to claim 1, wherein the cannister contains the following formulation having the following ingredients in the % by weights as indicated:

Fenoterol hydrobromide 0.192% by weight;
Absolute ethanol 30.000% by weight;
1,1,1,2 – tetrafluoroethane 67.806% by weight;
Citric acid 0.002% by weight; and
Purified water 2.000 % by weight. --

This certificate supercedes Certificate of Correction issued March 22, 2005.

Signed and Sealed this

Sixteenth Day of August, 2005

JON W. DUDAS
*Director of the United States Patent and Trademark Office*